US012257351B2

(12) United States Patent
McLaughlin et al.

(10) Patent No.: US 12,257,351 B2
(45) Date of Patent: *Mar. 25, 2025

(54) MINIMIZING AERATION OF SUSPENSIONS DURING IN-LINE MIXING

(71) Applicant: Catalent U.K. Swindon Zydis Limited, Swindon (GB)

(72) Inventors: Rosaleen McLaughlin, Swindon (GB); Simon Andrew Martyn Howes, Swindon (GB); Jonathon Whitehouse, Swindon (GB)

(73) Assignee: Catalent U.K. Swindon Zydis Limited, Swindon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/798,067

(22) Filed: Feb. 21, 2020

(65) Prior Publication Data

US 2020/0268677 A1    Aug. 27, 2020

Related U.S. Application Data

(60) Provisional application No. 62/809,293, filed on Feb. 22, 2019.

(51) Int. Cl.
A61K 9/50      (2006.01)
A61K 45/06     (2006.01)

(52) U.S. Cl.
CPC .......... *A61K 9/5084* (2013.01); *A61K 9/5015* (2013.01); *A61K 9/5036* (2013.01); *A61K 9/5089* (2013.01); *A61K 45/06* (2013.01)

(58) Field of Classification Search
CPC .. A61K 9/5015; A61K 9/5036; A61K 9/5084; A61K 9/5089; A61K 45/06; A61K 9/0056; A61K 47/06; A61K 9/10; A61K 31/192; A61K 9/0053; A61K 9/2813; A61K 9/282; A61K 9/284; A61K 9/2886; A61K 9/5073; A61K 9/2081; A61K 9/2013; A61K 9/205; A61P 29/00
See application file for complete search history.

(56) References Cited

U.S. PATENT DOCUMENTS

| | | | |
|---|---|---|---|
| 4,305,502 A | 12/1981 | Gregory et al. | |
| 4,371,516 A | 2/1983 | Gregory et al. | |
| 4,758,598 A | 7/1988 | Gregory | |
| 5,008,117 A * | 4/1991 | Calanchi | A61K 9/5047 516/107 |
| 5,320,848 A | 6/1994 | Geyer | |
| 5,558,880 A | 9/1996 | Gole et al. | |
| 5,976,577 A | 11/1999 | Green et al. | |
| 6,214,386 B1 | 4/2001 | Santus | |
| 6,413,549 B2 | 7/2002 | Green et al. | |
| 6,509,040 B1 * | 1/2003 | Murray | A61K 9/0056 424/490 |
| 6,709,669 B1 | 3/2004 | Murray et al. | |
| 6,951,657 B1 | 10/2005 | Zuccarelli | |
| 9,107,851 B2 | 8/2015 | Dave et al. | |
| 11,166,919 B2 | 11/2021 | McLaughlin et al. | |
| 11,185,508 B2 | 11/2021 | McLaughlin et al. | |
| 2003/0185096 A1 * | 10/2003 | Hollstein | B01F 33/4532 366/273 |
| 2003/0195179 A1 * | 10/2003 | Sawa | A61P 37/06 514/174 |
| 2004/0137061 A1 | 7/2004 | Ishibashi et al. | |
| 2004/0170686 A1 * | 9/2004 | Fredrickson | A61K 9/0095 514/376 |
| 2004/0265373 A1 | 12/2004 | Wynn et al. | |
| 2007/0148099 A1 | 6/2007 | Burke et al. | |
| 2007/0292508 A1 | 12/2007 | Szamosi et al. | |
| 2008/0075825 A1 | 3/2008 | Fuisz et al. | |
| 2008/0096979 A1 | 4/2008 | Pilgaonkar | |
| 2008/0113021 A1 | 5/2008 | Shen | |
| 2008/0311201 A1 | 12/2008 | Der-Yang et al. | |
| 2008/0317853 A1 | 12/2008 | Kashid et al. | |
| 2009/0062241 A1 | 3/2009 | Bauer | |
| 2009/0148524 A1 | 6/2009 | Higuchi et al. | |
| 2011/0229573 A1 | 9/2011 | Tian | |
| 2014/0105936 A1 | 4/2014 | Limonov et al. | |
| 2014/0106059 A1 | 4/2014 | Dave et al. | |
| 2016/0361335 A1 | 12/2016 | Jacob et al. | |
| 2020/0268667 A1 | 8/2020 | McLaughlin et al. | |

(Continued)

FOREIGN PATENT DOCUMENTS

| CA | 2398288 A1 | 8/2001 |
|---|---|---|
| CA | 2512988 A1 | 8/2004 |

(Continued)

OTHER PUBLICATIONS

Deterre et al. J Essential Oil Research. 2014; 26(4): 254-262. (Year: 2014).*

Anonymous. Safety Data Sheet Orange Tincture. JML [online]; downloaded from <URL https://jmloveridge.com/wp-content/uploads/2018/06/Orange-Tincture-Version-06.pdf> on Mar. 24, 2022; 6 pages. (Year: 2014).*

Anonymous. Making Orange Tincture. The Boozy Blog [online]; 2013; downloaded from <URL https://boozyblog.wordpress.com/2013/08/05/making-orange-tincture/ > on May 24, 2023; 4 pages. (Year: 2013).*

(Continued)

*Primary Examiner* — David Browe
(74) *Attorney, Agent, or Firm* — Morrison & Foerster LLP

(57) ABSTRACT

Provided are methods of making a pharmaceutical composition comprising: providing a matrix solution/suspension comprising a matrix former, a structure former, 0.1-1.5 wt. % anti-aerating agent, and a solvent; mixing a plurality of hydrophobic particles into the matrix solution/suspension to form a pharmaceutical suspension; and dosing the pharmaceutical suspension into preformed blister packs, wherein a dosed weight of the dosed pharmaceutical suspension is within 10 % of a target dosed weight.

11 Claims, 4 Drawing Sheets

(56) References Cited

U.S. PATENT DOCUMENTS

| | | |
|---|---|---|
| 2020/0268668 A1 | 8/2020 | McLaughlin |
| 2020/0268676 A1 | 8/2020 | McLaughlin |
| 2020/0390704 A1 | 12/2020 | Mclaughlin |
| 2020/0390716 A1 | 12/2020 | Mclaughlin |
| 2023/0390205 A1 | 12/2023 | McLaughlin et al. |

FOREIGN PATENT DOCUMENTS

| | | | |
|---|---|---|---|
| CN | 102300558 | A | 12/2011 |
| CN | 102579390 | A | 7/2012 |
| CN | 103169655 | A | 6/2013 |
| CN | 104853751 | A | 8/2015 |
| EP | 0636365 | A1 | 2/1995 |
| EP | 1405635 | A1 | 4/2004 |
| EP | 1621186 | A1 | 2/2006 |
| GB | 211423 | A | 2/1924 |
| GB | 1548022 | A | 7/1979 |
| JP | H9-511256 | A | 11/1997 |
| JP | 2002-012557 | A | 1/2002 |
| JP | 2003-055197 | A | 2/2003 |
| JP | 2003-525223 | A | 8/2003 |
| JP | 2007-525413 | A | 9/2007 |
| JP | 2008-508255 | A | 3/2008 |
| JP | 2008-517979 | A | 5/2008 |
| JP | 2008-526827 | A | 7/2008 |
| JP | 2015-533162 | A | 11/2015 |
| JP | 2017-532331 | A | 11/2017 |
| TW | 512167 | B | 12/2002 |
| WO | 92/22369 | A1 | 12/1992 |
| WO | 01/54683 | A1 | 8/2001 |
| WO | 02/47607 | A2 | 6/2002 |
| WO | 2004/066925 | A2 | 8/2004 |
| WO | 2006/045830 | A1 | 5/2006 |
| WO | 2006/072832 | A1 | 7/2006 |
| WO | 2008/036299 | A2 | 3/2008 |
| WO | 2009/108775 | A2 | 9/2009 |
| WO | 2011/063531 | A1 | 6/2011 |
| WO | 2013/024373 | A1 | 2/2013 |
| WO | 2013/183062 | A2 | 12/2013 |
| WO | 2014/062444 | A1 | 4/2014 |
| WO | 2017/080566 | A1 | 5/2017 |
| WO | 2020/169989 | A1 | 8/2020 |

OTHER PUBLICATIONS

Andrews. How to Extract Oil from the Skin of Oranges. Week& [online]; 2018; downloaded from < URL https://www.weekand.com/healthy-living/article/extract-oil-skin-oranges-18009337.php > on May 24, 2023; 4 pages. (Year: 2018).*

Anonymous. How to Extract Oil from Orange Peels. Wiki [online]; 2017; downloaded from <URL https://web.archive.org/web/20170603094953/https://www.wikihow.com/Extract-Oil-from-Orange-Peels > on May 24, 2023; 5 pages. (Year: 2017).*

Bourgou et al. The Scientific World Journal. 2012; 2012: 528593. (Year: 2012).*

Jabri karoui et al. Biomed Res Int. 2013; 2013: 345415. (Year: 2013).*

McLaughlin et al., Office Action dated Apr. 12, 2021, directed to U.S. Appl. No. 16/797,927; 21 pages.

McLaughlin et al., Office Action dated Apr. 13, 2021, directed to U.S. Appl. No. 16/798,130; 29 pages.

Syloid FG Silica (2015) "Syloid 244 FP silica: Formulation of viscous Simethicone in to chewable tablets," located at https://www.pharmaexcipients.com/wp-content/uploads/attachments/AP010_Syloid+244+FP-Formulation+of +Simethicone+into+chewable+tablets_Final.pdf?t=1458129627. (2 pages).

McLaughlin et al., Office Action dated May 12, 2021, directed to U.S. Appl. No. 16/797,934; 22 pages.

Combined Search and Examination Report dated Nov. 22, 2021, directed to GB Application No. 2107172.5; 4 pages.

Combined Search and Examination Report dated Nov. 22, 2021, directed to GB Application No. 2107174.1; 4 pages.

Combined Search and Examination Report dated Nov. 22, 2021, directed to GB Application No. 2107177.4; 5 pages.

International Search Report and Written Opinion dated Nov. 5, 2021, directed to International Application No. PCT/IB2021/056976; 15 pages.

McLaughlin et al., Office Action dated Dec. 9, 2020, directed to U.S. Appl. No. 17/008,108; 22 pages.

O'Connell (May 2005). "Sieve Use in the Pharmaceutical Industry," Pharmaceutical Technology Europe 17(5): 7 pages.

McLaughlin et al., Office Action dated Dec. 7, 2020, directed to U.S. Appl. No. 17/008,318; 16 pages.

McLaughlin et al., Office Action dated Feb. 10, 2021, directed to U.S. Appl. No. 16/797,934; 24 pages.

Zhou et al. (Aug. 2013). "Improving manufacturability of an ibuprofen powder blend by surface coating with silica hanoparticles," Powder Technology 249: 290-296.

National Center for Biotechnology Information. (Apr. 28, 2006). "Compound Summary—Simethicone," located at https://pubchem.ncbi.nlm.nih.gov/compound/Simethicone (2 pages).

Combined Search and Examination Report dated Apr. 28, 2020, directed to GB Application No. 2002466.7; 5 pages.

Combined Search and Examination Report dated Apr. 28, 2020, directed to GB Application No. 2002475.8; 7 pages.

Combined Search and Examination Report dated Apr. 28, 2020, directed to GB Application No. 2002479.0; 8 pages.

Combined Search and Examination Report dated Apr. 28, 2020, directed to GB Application No. 2002484.0; 7 pages.

International Search Report and Written Opinion mailed Apr. 17, 2020, directed to International Application No. PCT/GB2020/050419; 15 pages.

International Search Report and Written Opinion mailed Apr. 20, 2020, directed to International Application No. PCT/GB2020/050420; 13 pages.

International Search Report and Written Opinion mailed Apr. 21, 2020, directed to International Application No. PCT/GB2020/050422; 14 pages.

International Search Report and Written Opinion mailed Apr. 21, 2020, directed to International Application No. PCT/GB2020/050423; 14 pages.

First Written Opinion dated Nov. 2, 2022, directed to SG Application No. 11202108659X; 8 pages.

First Written Opinion dated Nov. 2, 2022, directed to SG Application No. 11202109104X; 7 pages.

First Written Opinion dated Nov. 2, 2022, directed to SG Application No. 11202109022U; 8 pages.

First Written Opinion dated Nov. 3, 2022, directed to SG Application No. 11202108690Y; 11 pages.

Examination Report dated Feb. 6, 2023, directed to GB Application No. 2002466.7; 4 pages.

Examination Report dated Feb. 8, 2023, directed to GB Application No. 2107172.5; 3 pages.

McLauglin et al., U.S. Office Action dated Feb. 6, 2023, directed to U.S. Appl. No. 17/307,638; 17 pages.

Office Action dated Feb. 14, 2023, directed to GB Application No. 2002475.8; 3 pages.

Office Action dated Feb. 22, 2023, directed to IN Application No. 202127042578; 5 pages.

Office Action dated Feb. 27, 2023, directed to EP Application No. 20708584.6; 5 pages.

First Office Action dated Nov. 3, 2022, directed to CN Application No. 202080015446.5; 22 pages.

Evonik-Gleriri Corp. "Aerosil® R972," located at https://glenncorp.com/shop/aerosil-r-972/, retrieved on May 16, 2023. (1 page).

McLaughlin et al., U.S. Office Action dated Jun. 16, 2023, directed to U.S. Appl. No. 17/529,827; 26 pages.

McLaughlin et al., U.S. Office Action dated Jun. 8, 2023, directed to U.S. Appl. No. 17/390,331; 11 pages.

McLaughlin et al., U.S. Office Action dated May 15, 2023, directed to U.S. Appl. No. 17/387,803; 18 pages.

Office Action dated Jul. 10, 2023, directed to RU Application No. 2021127592; 37 pages.

Office Action dated Jul. 11, 2023, directed to MX Application No. 2021-009845; 6 pages.

(56) References Cited

OTHER PUBLICATIONS

Office Action dated Jul. 12, 2023, directed to RU Application No. 2021127591; 25 pages.
Office Action dated Jul. 14, 2023, directed to RU Application No. 2021127588; 22 pages.
Office Action dated Jul. 28, 2023, directed to IN Application No. 2021-27042579; 8 pages.
Office Action dated Jun. 1, 2023, directed to GB Application No. 2107172.5; 1 page.
Office Action dated Jun. 23, 2023, directed to MX Application No. MX/a/2021/009679; 6 pages.
Office Action dated Jun. 27, 2023, directed to MX Application No. MX/a/2021/009681; 6 pages.
Office Action dated May 2, 2023, directed to IN Application No. 202127042581; 6 pages.
Office Action dated May 22, 2023, directed to CN Application No. 202080015446.5; 8 pages.
Office Action dated May 31, 2023, directed to GB Application No. 2002466.7; 1 pages.
Office Action dated May 31, 2023, directed to GB Application No. 2002475.8; 2 pages.
Office Action dated May 31, 2023, directed to IN Application No. 202127042580; 6 pages.
McLaughlin et al., U.S. Office Action dated Dec. 7, 2023, directed to U.S. Appl. No. 17/390,331; 6 pages.
Office Action dated Dec. 11, 2023, directed to RU Application No. 2021127590; 24 pages.
Office Action dated Dec. 6, 2023, directed to RU Application No. 2021127592; 17 pages.
Office Action dated Dec. 7, 2023, directed to RU Application No. 2021127591; 14 pages.
Office Action dated Nov. 17, 2023, directed to MX Application No. MX/a/2021/009844; 6 pages.
Office Action dated Nov. 3, 2023, directed to TW Application No. 109105770; 8 pages.
Extended European search report dated Dec. 18, 2023, directed to EP Application No. 23183926.7; 8 pages.
First Office Action dated Dec. 27, 2023, directed to CN Application No. 202080015572.0; 34 pages.
Notice of Reasons for Rejection dated Dec. 4, 2023, directed to JP Application No. 2021-549375; 11 pages.
Office Action dated Dec. 12, 2023, directed to RU Application No. 2021127588; 16 pages.
Office Action dated Nov. 1, 2023, directed MX Application No. MX/a/2021/009845; 11 pages.
Office Action dated Nov. 4, 2023, directed to CN Application No. 202080015635.2; 23 pages.
Office Action dated Nov. 7, 2023, directed to TW Application No. 109105773; 10 pages.
Office Action dated Nov. 8, 2023, directed to TW Application No. 109105762; 10 pages.
Office Action dated Nov. 9, 2023, directed to CN Application No. 202080015564.6; 28 pages.
Office Action dated Jul. 13, 2023, directed to RU Application No. 2021127590; 30 pages.
Chueshov et al. (2002). Industrial Drug Technology. vol. 2; pp. 352-355.
Pertsev et al. (1999). Pharmaceutical and biomedical aspects of drugs, vol. 1; pp. 253-254.
McLaughlin et al., U.S. Office Action dated Sep. 13, 2023, directed to U.S. Appl. No. 17/387,803; 10 pages.
McLaughlin et al., U.S. Office Action dated Sep. 13, 2023, directed to U.S. Appl. No. 17/529,827; 15 pages.
Office Action dated Aug. 9, 2023, directed to MX Application No. MX/a/2021/009844; 5 pages.
Office Action dated Jul. 18, 2023, directed to TW Application No. 109105762; 14 pages.
Office Action dated Jul. 26, 2023, directed to TW Application No. 109105759; 12 pages.
Office Action dated Oct. 9, 2023, directed to MX Application No. MA/a/2021/009681; 9 pages.
Office Action dated Sep. 13, 2023, directed to MX Application No. MX/a/2021/009679; 10 pages.
Office Action dated Sep. 28, 2023, directed to PH Application No. 1/2021/552022; 4 pages.
Third Office Action dated Sep. 18, 2023, directed to CN Application No. 202080015446.5; 10 pages.
Bikiaris et al., (2007). "New Aspects in Sustained Drug Release Formulations," Recent Patents on Drug Delivery & Formulation 1(3): 201-213.
Extended European Search Report dated Jan. 23, 2024, directed to EP Application No. 23186234.3; 10 pages.
Extended European Search Report dated Jan. 31, 2024, directed to EP Application No. 23189317.3; 16 pages.
Gad, 2005. "Limonene," Encyclopedia of Toxicology (Second Edition), pp. 720-725.
Office Action dated Dec. 7, 2023, directed to TW Application No. 109105759; 8 pages.
Office Action dated Jan. 30, 2024, directed to MX Application No. MX/a/2021/009679; 9 pages.
Office Action dated Jan. 9, 2024, directed to JP Application No. 2021-549372; 9 pages.
Office Action dated Jan. 9, 2024, directed to JP Application No. 2021-549373; 12 pages.
Subsequent Substantive Examination Report dated Jan. 12, 2024, directed to EP Application No. 1/2021/552022; 4 pages.
McLaughlin et al., U.S. Office Action dated Mar. 4, 2024, directed to U.S. Appl. No. 17/529,827; 19 pages.
Office Action dated Apr. 18, 2024, directed to IL Application No. 285653; 4 pages.
Office Action dated Apr. 22, 2024, directed to MX Application No. MX/a/2021/009845; 5 pages.
Office Action dated Feb. 22, 2024, directed to MX Application No. MX/a/2021/009681; 8 pages.
Office Action dated Mar. 11, 2024, directed to JP Application No. 2021-549374; 11 pages.
Office Action dated Mar. 21, 2024, directed to IL Application No. 285640; 4 pages.
Office Action dated Mar. 27, 2024, directed to IL Application No. 285648; 4 pages.
Office Action dated Mar. 4, 2024, directed to IN Application No. 202127042580; 3 pages.
Office Action dated Mar. 5, 2024, directed to MX Application No. MX/a/2021/009844; 7 pages.
Office Action dated May 9, 2024, directed to MX Application No. MX/a/2021/2021009679; 10 pages.
Decision of Rejection dated Jul. 8, 2024, directed to JP Application No. 2021-549375; 7 pages.
Huang et al., (2017). "Improving blend content uniformity via dry particle coating of micronized drug powders," European Journal of Pharmaceutical Sciences 104: 344-355.
McLaughlin et al., U.S. Office Action dated Jul. 25, 2024, directed to U.S. Appl. No. 17/529,827; 23 pages.
Office Action dated Aug. 13, 2024, directed to JP Application No. 2021-549374; 5 pages.
Office Action dated Aug. 27, 2024, directed to BR Application No. 112021016405-7; 5 pages.
Office Action dated Aug. 30, 2024, directed to CN Application No. 202080015564.6; 28 pages.
Office Action dated Jul. 26, 2024, directed to CN Application No. 202080015635.2; 14 pages.
Office Action dated Jun. 18, 2024, directed to MX Application No. MX/a/2021/009681; 11 pages.
Office Action dated May 6, 2024, directed to TW Application No. 109105773; 9 pages.
Office Action dated May 7, 2024, directed to CN Application No. 202180051278.X; 20 pages.
Office Action dated Oct. 1, 2024, directed to AU Application No. 2020223894; 3 pages.
Office Action dated Sep. 24, 2024, directed to AU Application No. 2020225818; 3 pages.

(56) References Cited

OTHER PUBLICATIONS

Office Action dated Sep. 26, 2024, directed to AU Application No. 2020225448; 4 pages.
Second Office Action dated Aug. 29, 2024, directed to CN Application No. 202080015572.0; 39 pages.

* cited by examiner

MINIMIZING AERATION OF SUSPENSIONS DURING IN-LINE MIXING

CROSS REFERENCE TO RELATED APPLICATIONS

This application claims the priority of U.S. Provisional Application No. 62/809,293, filed Feb. 22, 2019, the entire contents of which are incorporated herein by reference.

FIELD OF THE INVENTION

This relates to compositions and methods for preparing compositions that can minimize the aeration of pharmaceutical suspensions of hydrophobic particulates, and more particularly, to compositions and methods of preparing compositions that can minimize the aeration of the pharmaceutical suspensions of coated active pharmaceutical ingredients (APIs) for improved dose weight accuracy whilst maintaining the integrity of the functional coat on the APIs particles.

BACKGROUND OF THE INVENTION

Pharmaceutical compositions typically include both an active pharmaceutical ingredient as well as one or more inactive ingredients. The active pharmaceutical ingredient (API) is biologically active and is designed to directly affect a patient's symptoms, diseases, disorders, and/or ailments. The inactive ingredient(s) of a pharmaceutical composition, on the other hand, are pharmaceutically inert and can be used for various purposes including, but not limited to, improving long-term stabilization, filling or diluting a solid formulation, facilitating drug absorption, modifying viscosity of liquid formulations, enhancing solubility and/or aiding the manufacture of the pharmaceutical composition.

One type of pharmaceutical composition is an orally-disintegrating tablet (ODT). ODTs are pharmaceutical compositions targeted to pediatric patients, geriatric patients, animal patients, and/or other types of patients that may have difficulties swallowing. For these types of orally-administered pharmaceutical composition, inactive ingredients may be used to mask the taste of the API.

Coating can be used for masking the taste of a pharmaceutical composition by coating a tablet containing API or by directly coating the API particles themselves. An inactive ingredient may be used to mask the taste of the API by wet coating or dry coating of the API to produce a functional coating surrounding the API particles such that it prevents API release in oral cavity. In wet particle coating, inactive ingredients (polymers and additives) are dissolved or dispersed in solvent or water to form a suspension or solution. This suspension or solution can be sprayed onto the surface of the API particles to form a coating film by evaporation of the solvent or water. Examples of technologies for wet particle coating include microencapsulation, fluid bed coating, solvent evaporation, spray drying, pan coating etc. In dry particle coating (also referred to as solventless coating), API particles are mechanically coated with fine particles of inactive ingredients (polymers and additives) to form particle composites. Examples of dry particle coating include hot melt coating, supercritical coating, impaction coating, electrostatic coating, etc. APIs particles coated with a taste-masking inactive ingredient may provide a more pleasant experience for a patient having difficulties swallowing or having a sensitivity to taste that would otherwise lead to a negative patient experience and poor compliance, in particular for pharmaceutical compositions that dissolve or disintegrate in the oral cavity. However, many of the materials used to coat APIs are hydrophobic. Thus, the coated API particles are hydrophobic.

To accurately dispense a pharmaceutical composition into a small, administrable form, a hydrophobic coated API particle can be placed in a matrix solution/suspension to form a pharmaceutical suspension. Mixing the API to form a pharmaceutical suspension allows for improved dosing accuracy. Oftentimes, this pharmaceutical suspension comprising the hydrophobic coated API particles can be dosed into molds, dried, and the molded article can then be transferred into a bottle, for example. However, this kind of handling of the pharmaceutical composition can increase risks such as damage and contamination.

Accordingly, many API suspensions today are dosed into preformed blister packs instead. Preformed blister packs eliminate one of the handling steps described above. Instead of dosing into a mold and then transferring the molded article to a bottle for packaging, preformed blister packs allow a manufacturer to dose the pharmaceutical suspension into a preformed blister pack that can be dried, then sealed and packaged. Thus, the preformed blister pack serves as both the mold and the package in which the pharmaceutical composition can be stored.

SUMMARY OF THE INVENTION

Provided are compositions and methods for preparing compositions that can minimize aeration of hydrophobic API particles in a pharmaceutical suspension. For example, hydrophobic coated API particles may be mixed into matrix solution/suspension to form a pharmaceutical suspension to accurately dose into molds to form solid pharmaceutical compositions (i.e., article, tablet, etc.) for administering to a patient. However, the hydrophobicity of the coated API particles causes the coated API particles to resist dispersing into the matrix solution/suspension. Consequently, this can cause air to become entrained with the pharmaceutical suspension, also known as aeration. Entrained air, or aeration of the pharmaceutical suspension, can cause phase separation of the coated API particles in the pharmaceutical suspension, causing a non-homogenous pharmaceutical suspension. Aeration and non-homogeneous pharmaceutical suspension can lead to poor dose weight accuracy of the pharmaceutical suspension comprising the hydrophobic API particles dosed into preformed blister packs and poor content uniformity in the finished product (i.e., pharmaceutical composition).

Traditional mechanical means of anti-aeration and/or minimizing aeration have not been found to be successful due to the high viscosity of the pharmaceutical suspension. For example, minimizing aeration may be achieved by applying vacuum to a pharmaceutical suspension, but depending on the composition and further processing requirements this approach may not be suitable. In particular, applying a vacuum to the pharmaceutical suspension can cause the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, compositions and methods provided herein minimize the aeration of a pharmaceutical suspension comprising hydrophobic coated API particles to improve the homogeneity of the pharmaceutical suspension and increase the dose weight accuracy. Specifically, embodiments provided can include matrix solutions/suspensions comprising chemical compounds comprising terpene and/or terpinol. In some embodiments, a matrix solution/suspension may comprise the terpene limonene. By introducing a terpene-comprising chemical compound such as limonene, the hydrophobic coated API particles may more readily incorporate into the matrix solution/suspension, minimizing the overall aeration of the pharmaceutical suspension.

The solutions, suspensions, and compositions provided herein are described with respect to hydrophobic coated API particles. However, solutions, suspensions, and compositions and methods of preparing solutions, suspensions, and compositions provided herein may be used to minimize the aeration of any hydrophobic material that can be mixed into a pharmaceutical suspension. For example, other types of compositions may be mixed into the suspension composition according to some embodiments.

In some embodiments, a method of making a pharmaceutical composition is provided, the method comprising: providing a matrix solution/suspension comprising a matrix former, a structure former, an anti-aerating agent, and a solvent; and mixing a plurality of hydrophobic particles into the matrix solution/suspension to form a pharmaceutical suspension; and dosing the pharmaceutical suspension into preformed blister packs, wherein the dispensed or dosed weight of the dosed pharmaceutical suspension is within 10.0 percent of a target dosed weight. In some embodiments of the method, the dispensed weight percentage of the dosed pharmaceutical suspension is within 5.0 percent of a target dosed weight. In some embodiments of the method, the dispensed weight of the dosed pharmaceutical suspension is within 2.5 percent of a target dosed weight. In some embodiments of the method, the dispensed weight of the dosed pharmaceutical suspension is within 1.0 percent of a target dosed weight. In some embodiments of the method, the plurality of hydrophobic particles comprises coated active pharmaceutical ingredient (API). In some embodiments of the method, the coated API comprise one or more of anti-inflammatories, analgesics, anti-psychotics, anti-emetics, laxatives, anti-diarrheals, anti-histamines, or anti-depressants. In some embodiments of the method, the composition of the functionally-coated API comprises from 30-90% w/w API. In some embodiments of the method, the matrix solution/suspension comprises a viscosity modifier. In some embodiments of the method, the viscosity modifier comprises xanthan gum. In some embodiments of the method, mixing a plurality of hydrophobic particles into the matrix solution/suspension comprises in-line mixing at 15-20° C. degrees Celsius. In some embodiments of the method, the anti-aerating agent comprises one or more of a terpene or a terpinol. In some embodiments of the method, the anti-aerating agent comprises a liquid flavor. In some embodiments of the method, the anti-aerating agent comprises a liquid flavor comprising limonene. In some embodiments of the method, the anti-aerating agent comprises one or more of orange flavor, lemon flavor, grapefruit flavor, lime flavor, strawberry flavor, or peppermint flavor. In some embodiments of the method, the matrix solution/suspension or the pharmaceutical suspension comprises from 0.1-1.5% w/w anti-aerating agent. In some embodiments of the method, the matrix solution/suspension or the pharmaceutical suspension comprises from 2.0-5.0% w/w matrix former. In some embodiments of the method, the matrix solution/suspension or the pharmaceutical suspension comprises from 1.0-5.0% w/w structure former.

In some embodiments, a pharmaceutical composition is provided, the pharmaceutical composition prepared by a process comprising the steps of: providing a matrix solution/suspension comprising a matrix former, a structure former, an anti-aerating agent, and a solvent; and mixing a plurality of hydrophobic particles into the matrix solution/suspension to form a pharmaceutical suspension; and dosing the pharmaceutical suspension into preformed blister packs, wherein the dispensed weight percentage of dosed the pharmaceutical suspension is within 10.0 percent of a target dosed weight. In some embodiments of the pharmaceutical composition, the dispensed weight of the dosed suspension is within 5.0 percent of a target dosed weight. In some embodiments of the pharmaceutical composition, the dispensed weight of the dosed suspension within 2.5 percent of a target dosed weight. In some embodiments of the pharmaceutical composition, the dispensed weight of the dosed suspension within 1.0 percent of a target dosed weight. In some embodiments of the pharmaceutical composition, the plurality of hydrophobic particles comprises coated active pharmaceutical ingredient (API). In some embodiments of the pharmaceutical composition, the coated API comprise one or more of one or more of anti-inflammatories, analgesics, anti-psychotics, anti-emetics, laxatives, anti-diarrheals, anti-histamines, or anti-depressants. In some embodiments of the pharmaceutical composition, the composition of the functionally-coated API comprises from 30-90% w/w API. In some embodiments of the pharmaceutical composition, the matrix solution/suspension comprises a viscosity modifier. In some embodiments of the pharmaceutical composition, the viscosity modifier comprises xanthan gum. In some embodiments of the pharmaceutical composition, mixing a plurality of hydrophobic particles into the matrix solution/suspension comprises in-line mixing at 15-20° C. degrees Celsius. In some embodiments of the pharmaceutical composition, the anti-aerating agent comprises one or more of a terpene or a terpinol. In some embodiments of the pharmaceutical composition, the anti-aerating agent comprises a liquid flavor. In some embodiments of the pharmaceutical composition, the anti-aerating agent comprises a liquid flavor comprising limonene. In some embodiments of the pharmaceutical composition, the anti-aerating agent comprises one or more of orange flavor, lemon flavor, grapefruit flavor, lime flavor, strawberry flavor, or peppermint flavor. In some embodiments of the pharmaceutical composition, the pharmaceutical composition comprises from 1-5% w/w anti-aerating agent. In some embodiments of the pharmaceutical composition, the pharmaceutical composition comprises from 3-10% w/w matrix former. In some embodiments of the pharmaceutical composition, the pharmaceutical composition comprises from 3-10% w/w structure former.

In some embodiments, a method of treating a patient is provided, the method comprising administering to a patient the pharmaceutical composition. In some embodiments of the method, the patient is a human.

In some embodiments, a pharmaceutical composition is provided, the pharmaceutical composition comprising: a plurality of API particles; a coating material encapsulating each API particle of the plurality of API particles; a matrix former; a structure former; and an anti-aerating agent. In some embodiments of the pharmaceutical composition, the pharmaceutical composition is formed by creating a matrix solution/suspension comprising the matrix former, the structure former, and the anti-aerating agent. In some embodiments of the pharmaceutical composition, the plurality of API particles comprises one or more of one or more of anti-inflammatories, analgesics, anti-psychotics, anti-emetics, laxatives, anti-diarrheals, anti-histamines, or anti-depressants. In some embodiments of the pharmaceutical composition, the matrix solution/suspension comprises a viscosity modifier. In some embodiments of the pharmaceutical composition, the viscosity modifier comprises xanthan gum. In some embodiments of the pharmaceutical composition, the anti-aerating agent comprises one or more of a terpene or a terpinol. In some embodiments of the pharmaceutical composition, the anti-aerating agent comprises a liquid flavor. In some embodiments of the pharmaceutical composition, the anti-aerating agent comprises a liquid flavor comprising limonene. In some embodiments of the pharmaceutical composition, the anti-aerating agent comprises one or more of orange flavor, lemon flavor, grapefruit flavor, lime flavor, strawberry flavor, or peppermint flavor. In some embodiments of the pharmaceutical composition, the composition of the functionally coated API comprises from 30-90% w/w API. In some embodiments of the pharmaceutical composition, the pharmaceutical composition comprises from 1-5% w/w anti-aerating agent. In some embodiments of the pharmaceutical composition, the pharmaceutical composition comprises from 3-10% w/w matrix former. In some embodiments of the pharmaceutical composition, the pharmaceutical composition comprises from 3-10% w/w structure former.

BRIEF DESCRIPTION OF THE DRAWINGS

The invention will now be described, by way of example only, with reference to the accompanying drawings, in which.

DETAILED DESCRIPTION OF THE INVENTION

Figure 1:
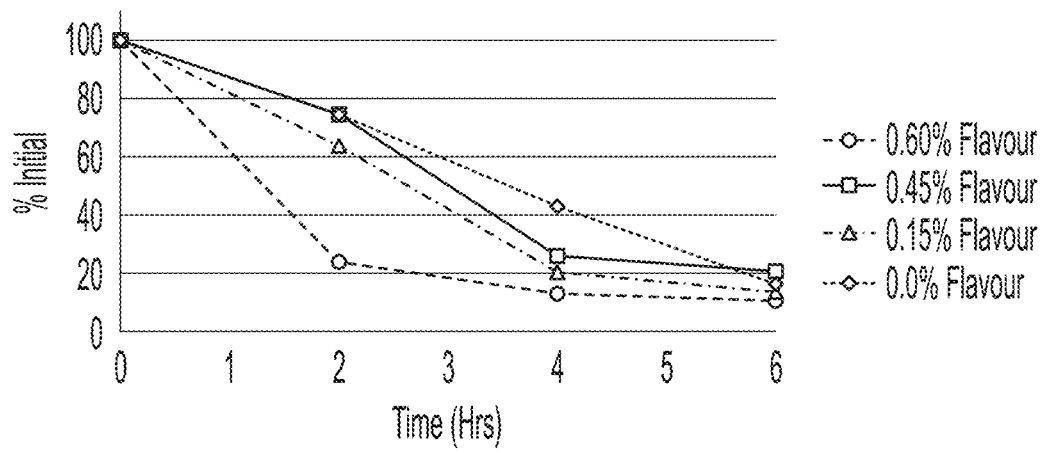
FIG. 1 shows a graph providing an evaluation of d10 particle size of hydrophobic coated API particles with various concentrations of liquid flavor.

Described herein are exemplary embodiments of compositions formulated to minimize the aeration of pharmaceutical suspensions comprising hydrophobic coated API particles. Also provided are methods of minimizing the aeration of pharmaceutical suspensions comprising hydrophobic coated API particles. In some embodiments, embodiments provided herein may include adding a chemical compound comprising terpene and/or terpinol to the matrix solution/suspension. Specifically, embodiments of suspensions provided herein may include liquid flavors comprising terpene and/or terpinols. In some embodiments, the liquid flavor(s) may include the terpene limonene. Particular chemical compounds, and specifically the addition of liquid flavors comprising limonene, can minimize the aeration of the pharmaceutical suspension, increase the homogeneity of the pharmaceutical suspension, and improve the dose weight accuracy when the pharmaceutical suspension is injected into molds. As used herein, "dose weight accuracy" and related terms refer to the ability to accurately dispense a pharmaceutical suspension into a pre-formed mold. The dose weight accuracy of a pharmaceutical suspension may depend on a number of variables, including, but not limited to, homogeneity, viscosity, chemical components, dosing instrument, etc.

As described above, traditional mechanical means of anti-aeration and/or minimizing aeration have not been found to be successful due to the high viscosity of the pharmaceutical suspension. For example, applying a vacuum to the suspension can cause a height of the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, it has been discovered that some chemical compounds, and in particular, liquid flavors comprising terpenes and/or terpinols such as limonene, can minimize the aeration of the pharmaceutical suspension when hydrophobic coated API particles are mixed into the matrix solution/suspension. By minimizing aeration, the hydrophobic coated API particles are more efficiently and effectively dispersed throughout the pharmaceutical suspension. This increased dispersion can increase the homogeneity of the suspension, the dose weight accuracy, as well as the content uniformity of the finished product.

In some embodiments, the coated API particles or pharmaceutical composition may comprise from 30.0 to 90.0% w/w API. In some embodiments, the coated API particles or pharmaceutical composition may comprise from 40.0 to 85.0% w/w, from 50.0 to 80.0% w/w, or from 70.0 to 80.0% w/w API. In some embodiments, the coated API particles or pharmaceutical composition may comprise more than 40.0% w/w, more than 50.0% w/w, more than 60.0% w/w, more than 65% w/w, more than 70.0% w/w, more than 75.0% w/w, more than 80.0% w/w, or more than 85.0% w/w API. In some embodiments, the coated API particles or pharmaceutical composition may comprise less than 90.0% w/w, less than 85.0% w/w, less than 80.0% w/w, less than 75.0% w/w, less than 70.0% w/w, less than 60.0% w/w, less than 50.0% w/w, or less than 40.0% w/w API.

Compositions and methods provided for minimizing the aeration of pharmaceutical suspensions according to embodiments described herein may be used with hydrophobic coated API particles prepared by solventless mixing processes. Accordingly, some embodiments provided below are described below in context of pharmaceutical suspensions comprising one or more hydrophobic coated API particles prepared by solventless mixing processes. However, one having skill in the art can readily recognize other applications of disclosed methods for minimizing the aeration of suspensions. For example, different mixing processes that can be used to coat, or encapsulate, an API with an inactive ingredient include sugar coating, film coating, other variations of microencapsulation, compression coating, other variations of dry coating, melting coating, dip coating, rotary die coating, electrostatic coating, and/or other suitable types of coating.

As described above, mixing hydrophobic coated API particles into a matrix solution/suspension can generate entrained air, or air bubbles in the liquid. Because the coated API particles are hydrophobic, they have a generally low affinity for the matrix solution/suspension. Thus, instead of readily associating with and dispersing into the matrix solution/suspension, the hydrophobic coated API particles preferably associate with the entrained air. In many fluids, air bubbles typically travel to the surface of the fluid and disappear into the air above. However, because the hydrophobic coated API particles have an affinity for the entrained air, the hydrophobic coated API particles "hold onto" the air bubbles, preventing them from traveling to the surface and releasing into the air above the fluid. This causes to the pharmaceutical suspension to become aerated. Aeration of the suspension can cause phase separation, and thus, a non-homogeneous pharmaceutical suspension. The phase separation can also become exaggerated upon exposure to shear forces introduced by dosing pumps. Non-homogenous pharmaceutical suspensions can cause pump seizures when passed through dosing pumps, leading to inaccurate dose weights and a lack of uniformity throughout the finished product as well as poor production efficiency through stoppages.

Additionally, pharmaceutical suspensions comprising hydrophobic coated API particles can have high viscosities due to a high loading of hydrophobic coated API particles (i.e., as much as 50 wt. % hydrophobic coated API particles). Entraining air into the suspension during in-line mixing of the hydrophobic coated API particles into suspension, as described above, can increase the viscosity of the suspension even further. Accordingly, not only does the phase separation and non-homogeneity of the pharmaceutical suspension adversely impact the dose weight accuracy and uniformity of the final product (i.e., pharmaceutical composition), but so too does the increased viscosity.

Interestingly, it has been found that certain chemical compounds, when added to the matrix solution/suspension, can minimize the aeration of pharmaceutical suspensions comprising hydrophobic coated API particles. Particularly, chemical compounds comprising terpene and/or terpinol, according to some embodiments provided herein, may minimize the amount of the entrained air in suspensions caused by in-line mixing of hydrophobic coated API particles into matrix solutions/suspensions. For example, matrix solutions/suspensions comprising liquid flavors comprising terpenes and/or terpinols, even in relatively low concentrations, can minimize aeration of pharmaceutical suspensions. Specifically, it has been discovered that matrix solutions/suspensions comprising one or more liquid flavor comprising limonene can minimize aeration in pharmaceutical suspensions during in-line mixing of hydrophobic coated API particles. Other chemical compounds including terpenes and terpinols have been shown to be successful at minimizing aeration of suspensions as well. For example, chemical compounds including terpenes such as limonene, carvone, humulene, taxadiene, and squalene may be suitable for minimizing the aeration of the suspension. Terpinol may also be a suitable anti-aerating agent. In some embodiments, pure terpenes and/or pure terpinols may be used as an anti-aerating agent. In some embodiments, a liquid flavor comprising terpene and/or terpinol may be used as an anti-aerating agent. In some embodiments, other suitable chemical compounds comprising terpene and/or terpinol may be used as an anti-aerating agent.

As used herein, "active pharmaceutical ingredient" or "API" refers to a drug product that may be used in the diagnosis, cure, mitigation, treatment, or prevention of disease. Any API may be used for purposes of the present disclosure. Suitable APIs include, without limitation: analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, antihypertensive agents, anti-malarials, anti-migraine agents, anti-muscarinic agents, anti-neoplastic agents and immunosuppressants, anti-protazoal agents, anti-psychotics, anti-emetics, antirheumatics, anti-thyroid agents, antivirals, anxiolytics, aperients, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, laxatives, lipid regulating agents, local anesthetics, neuromuscular agents, nitrates and anti-anginal agents, nutritional agents, opioid analgesics, oral vaccines, proteins, peptides and recombinant drugs, purgatives, sex hormones and contraceptives, spermicides, and stimulants; and combinations thereof. A list of specific examples of these API may be found in U.S. Pat. No. 6,709,669, which is incorporated herein by reference. When present, the API is present in the pharmaceutical formulation in an amount that is necessary to exhibit the required physiological effect as established by clinical studies. One of ordinary skill in the art can readily determine an appropriate amount of API to include in the dosage form made according to the present disclosure. Additionally, the compositions and methods of preparing the compositions provided herein are not limited to the above-listed APIs. The aeration behavior described herein is independent of the API because the matrix solution/suspension interacts with the coating of the API, not the API itself.

One challenge posed with some chemical compounds comprising terpene and/or terpinol, such as some liquid flavors, is that they tend to be relatively oily. As with conventional oil and water, these oily chemical compounds may not readily disperse into a matrix solution/suspension. However, as discussed below, matrix solutions/suspensions according to embodiments here may include gelatin as a matrix former. Gelatin is inherently a mild surfactant. Surfactants can lower the surface tension between two materials. Accordingly, in some embodiments, the gelatin of the matrix solution/suspension can reduce the surface tension between the oily chemical compounds and the matrix solution/suspension. This can allow adequate incorporation of the oily chemical compounds, such as liquid flavors, into the matrix solution/suspension.

Under normal processing conditions, without use of chemical compounds comprising terpene and/or terpinol, the coating of the hydrophobic coated API particles erodes with time due to shear forces required to mix the hydrophobic coated API particles into the matrix solution/suspension. However, there is a "processing window" of two or more hours wherein the coating retains significant functionality. The exact time of this "processing window" varies for each product, and can depend upon the composition of the components of the hydrophobic coated API particles, the composition of the matrix solution/suspension, the amount of material used to prepare the hydrophobic coated API particles, the physicochemical properties of the API, and/or the conditions of mixing. Unfortunately, in the presence of chemical compounds comprising terpenes and/or terpinols this "processing window" can be significantly reduced due to interactions between these chemical compounds and the coating of the hydrophobic coated API particles. These interactions may damage the functional properties of the coating. For example, interactions between liquid flavors and the coating of the hydrophobic coated API particles may damage any taste-masking functionality of the coating. That said, it has been discovered that there is a threshold chemical compounds (i.e., liquid flavor) concentration below which the chemical compound does not significantly compromise the coating, yet the "processing window" is not reduced so much that the coating of the hydrophobic coated API particles significantly erodes. Accordingly, this optimal amount of chemical compound comprising terpene and/or terpinol adequately minimizes the aeration of the suspension, resulting in a homogenous pharmaceutical suspension that can be accurately dosed into molds to yield a uniform final product.

Additionally, chemical compounds comprising terpene and/or terpinol, and specifically liquid flavors comprising limonene, have the potential to lower the freezing point of the pharmaceutical suspension, which could lead to melting defects for products further processed by freeze-drying. In particular, limonene has a freezing point of $-74°$ C. However, no melting defects have been observed during the preparation of the disclosed product, and thus at least some chemical compounds comprising terpene and/or terpinol do not impact the suspension such that the freezing and freeze-drying process steps downstream are adversely affected. The absence of melting defects under the present circumstances is believed to be due to the high solids content of the pharmaceutical suspension, which helps to maintain the structure of the product, even in the presence of a freezing point depressing agent (i.e., limonene).

Matrix solutions/suspensions according to embodiments described herein may include a matrix former, a structure former, an anti-aerating agent, a viscosity modifier, and/or a solvent.

In some embodiments, an amount of a chemical compounds comprising terpene and/or terpinol (i.e., an anti-aerating agent) in the matrix solution/suspension, the pharmaceutical suspension, or the pharmaceutical composition may be from 0.001 to 5.0% w/w. In some embodiments, an amount of chemical compounds comprising terpene and/or terpinol (i.e., an anti-aerating agent) in the matrix solution/suspension, the pharmaceutical suspension, or the pharmaceutical composition can be 1-5% w/w, 1-4% w/w, 1-3% w/w, 1-2% w/w, 0.05 to 3.0% w/w, 0.1 to 2.0% w/w, or 0.5 to 1.0% w/w. In some embodiments, more than 0.001% w/w, more than 0.01% w/w, more than 0.05% w/w, more than 0.1% w/w, more than 0.3% w/w, more than 0.5% w/w, more than 0.8% w/w, more than 1.0% w/w, more than 1.5% w/w, more than 2.0% w/w, more than 2.5% w/w, more than 3.0% w/w, more than 3.5% w/w, more than 4.0% w/w, or more than 4.5% w/w of chemical compounds comprising terpene and/or terpinol (i.e., an anti-aerating agent) are in the matrix solution/suspension, the pharmaceutical suspension, or the pharmaceutical composition. In some embodiments, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, less than 0.8% w/w, less than 0.6% w/w, less than 0.3% w/w, or less than 0.1% w/w of chemical compounds comprising terpene and/or terpinol (i.e., an anti-aerating agent) are in the matrix solution/suspension, the pharmaceutical suspension, or the pharmaceutical composition. In some embodiments, a suitable anti-aerating agent may include orange flavor, strawberry flavor, mint flavor, raspberry flavor, licorice flavor, orange flavor, lemon flavor, lime flavor, grapefruit flavor, caramel flavor, vanilla flavor, cherry flavor, grape flavor, mixed fruit flavor, tutti-frutti flavor or any combination thereof.

The matrix former of a matrix solution/suspension according to some embodiments may include any water soluble or water dispersable material that is pharmacologically acceptable or inert to the hydrophobic coated API particles. In some embodiments, the matrix former may be a polypeptide such as gelatin. The gelatin may be at least partially hydrolyzed (by heating in water). Other suitable matrix former materials include, but are not limited to, polysaccharides such as hydrolyzed dextran, dextrin, and alginates, polyvinyl alcohol, polyvinylpyrrolidone, and/or acacia. In some embodiments, the amount of matrix former in the matrix solution/suspension or pharmaceutical suspension can be from about 0.1 to 10% w/w. In some embodiments, the amount of matrix former in the matrix solution/suspension or pharmaceutical suspension may include from 1.0 to 8.0% w/w or from 2.0 to 5.0% w/w. In some embodiments, the amount of matrix former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of matrix former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of matrix former in a pharmaceutical composition can be about 3-15% w/w, about 4-10% w/w, or about 4-7% w/w. In some embodiments, the amount of matrix former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of matrix former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

A structure former, or bulking agent, of the matrix solution/suspension according to some embodiments may include a sugar. For example, suitable structure formers include, but are not limited to, mannitol, dextrose, lactose, galactose, glycine, cyclodextrin, or combinations thereof. The structure former can be used in freeze drying as a bulking agent as it crystallizes to provide structural robustness to the freeze-dried dosage form. In some embodiments, the amount of structure former in the matrix solution/suspension or pharmaceutical suspension can be from about 0.1 to 10% w/w. In some embodiments, the amount of structure former in the matrix solution/suspension or pharmaceutical suspension may include from 1.0 to 8.0% w/w or from 2.0 to 5.0% w/w. In some embodiments, the amount of structure former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of structure former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of structure former in a pharmaceutical composition can be about 3-15% w/w, about 4-10% w/w, or about 4-7% w/w. In some embodiments, the amount of structure former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of structure former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

In some embodiments, a matrix solution/suspension and pharmaceutical suspension may include a viscosity modifier. For example, a viscosity modifier according to embodiments provided herein may include vegetable gums such as xanthan gum, alginin, guar gum, or locust bean gum, proteins such as collagen or gelatin, sugars such as agar, carboxymethyl cellulose, pectin, or carrageenan, starches such as arrowroot, cornstarch, katakuri starch, potato starch, sago, or tapioca, and/or other suitable viscosity modifiers. In some embodiments, the amount of viscosity modifier in the matrix solution/suspension, pharmaceutical suspension, or the pharmaceutical composition may be from 0 to 0.2% w/w or from 0.01 to 0.1% w/w. In some embodiments, the amount of viscosity modifier in the matrix solution/suspension, pharmaceutical suspension, or the pharmaceutical composition may be greater than 0.01% w/w, greater than 0.03% w/w, greater than 0.05% w/w, greater than 0.07% w/w, greater than 0.1% w/w, greater than 0.12% w/w, greater than 0.15% w/w, or greater than 0.17% w/w. In some embodiment, the amount of viscosity modifier in the matrix solution/suspension, pharmaceutical suspension, or the pharmaceutical composition may be less than 0.2% w/w, less than 0.18% w/w, less than 0.15% w/w, less than 0.12% w/w, less than 0.1% w/w, less than 0.08% w/w, less than 0.06% w/w, or less than 0.03% w/w.

The solvent of the suspension/solution and pharmaceutical suspension may be water, but the suspension/solution may include a cosolvent as well. In some embodiments, the solvent can be ethanol, alcohol, isopropanol, other lower alkanols, water (e.g., purified water), or combinations thereof. For example, a suitable solvent and/or cosolvent may be an alcohol, such as tert-butyl alcohol. In some embodiments, the balance remaining of the pharmaceutical formulation is the solvent (i.e., Q.S. 100%).

The matrix solution/suspension and pharmaceutical suspension may also contain additional pharmaceutically acceptable agents or excipients. Such additional pharmaceutically acceptable agents or excipients include, without limitation, sugars, inorganic salts, such as sodium chloride and aluminum silicates, modified starches, preservatives, antioxidants, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include aspartame, acesulfame K, sucralose and thaumatin, and combinations thereof. Suitable taste-masking agents can include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

In some embodiments, a pharmaceutical suspension may be prepared by mixing API with one or more coating material at a temperature of 10-40, 15-25, or 15-20 degrees Celsius. In some embodiments, the materials may be mixed at a temperature of less than 40, less than 35, less than 30, less than 25, less than 20, or less than 15 degrees Celsius. In some embodiments, the materials may be mixed at a temperature of greater than 10, greater than 15, greater than 20, greater than 25, greater than 30, or greater than 35 degrees Celsius. In some embodiments, the materials may be mixed using a PharmaRAM II acoustic mixer, a RAM 5 Pharma acoustic mixer, or a RAM 55 Pharma mixer (Resodyn Mixers).

A pharmaceutical composition may be prepared by dosing the pharmaceutical suspension into preformed blister packs. In some embodiments, a freeze-dried orally disintegrating tablet may be prepared by dosing the pharmaceutical suspension into blister packs. In some embodiments, dosing pumps pump by volume, but the process is controlled by weight. Thus, to ensure content uniformity from one dosage form to the next, the dosing process may be controlled such that the volume-to-weight percentage of dosed suspension or the dispensed weight of the dosed pharmaceutical suspension is consistent. For example, a volume-to-weight percentage may be consistent within 10 percent, within 8 percent, within 6 percent, within 5 percent, within 4 percent, within 3 percent, within 2 percent, within 1.5 percent, within 1 percent, within 0.5 percent, or within 0.25 percent. In some embodiments, the weight of the dosed pharmaceutical suspension is within 10 percent, within 8 percent, within 6 percent, within 5 percent, within 4 percent, within 2.5 percent, within 2 percent, within 1.5 percent, within 1 percent, within 0.5 percent, or within 0.25 percent of a target dosed weight. Additionally, the viscosity of the suspension should be kept low enough for ease of dosing. As described above, a high viscosity of the suspension can case pump seizures during dosing.

In some embodiments, each dosage form of the pharmaceutical composition meets the content uniformity requirements of the United States Pharmacopeia. In some embodiments, each dosage form of the pharmaceutical composition meets the product quality requirements of the United States Pharmacopeia (e.g., volatile content, disintegration, tablet breaking force, uniformity of dosage units, etc.).

EXAMPLES

The effectiveness of chemical compounds comprising terpene and/or terpinol at minimizing aeration can be determined in part by measuring the particle size of the hydrophobic coated API particles in pharmaceutical suspension over time. If the chemical compound is effective, the aeration of the suspension will be adequately low and the particle size of the hydrophobic coated API particles will remain constant or decrease very little over time. If ineffective, the aeration of the pharmaceutical suspension will be higher than desired and the particle size of the hydrophobic coated API particles can decrease more substantially over time. The extent of aeration of the pharmaceutical suspension is assessed by measurement of height of the foam in the mixing vessel. The particle size of the functionally-coated particles can be measured using laser diffraction, a particle analyzer such as a Malvern Mastersizer, or any other suitable means for analyzing fine particles.

Example 1

A series of suspension mixes were manufactured by mixing the coated API in the matrix solution/suspension containing various levels of limonene, orange flavor, and strawberry flavor. The height of the foam from these suspensions is summarized in Table 1, 2 and 3 respectively.

TABLE 1

Height of foam from mixes containing various levels of limonene.

| Concentration of limonene (% w/w) | Foam Height (mm) |
|---|---|
| 0 | 5 |
| 0.15 | 2 |
| 0.30 | 1 |
| 0.6 | 1 |

TABLE 2

Height of foam from mixes containing various levels of orange flavor.

| Concentration of orange flavor (% w/w) | Foam Height (mm) |
|---|---|
| 0 | 5 |
| 0.15 | 1 |
| 0.30 | 0 |
| 0.6 | 0 |

TABLE 3

Height of foam from mixes containing various levels of strawberry flavor.

| Concentration of strawberry flavor (% w/w) | Foam Height (mm) |
|---|---|
| 0 | 5 |
| 0.15 | 3 |
| 0.30 | 3 |
| 0.6 | 3 |

The results in Tables 1 and 2 show that the addition of limonene and orange flavor at level 0.15% and above minimize the aeration. For strawberry (Table 3), it also reduced aeration but not to the same extent.

Example 2

Figure 2:
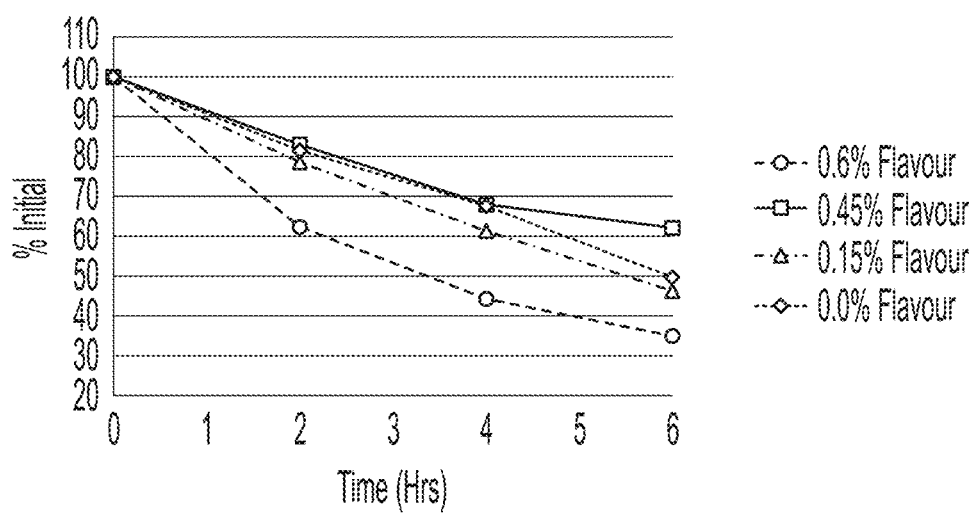
FIG. 2 shows a graph providing an evaluation of d50 particle size of hydrophobic coated API particles with various concentrations of liquid flavor.
Figure 3:
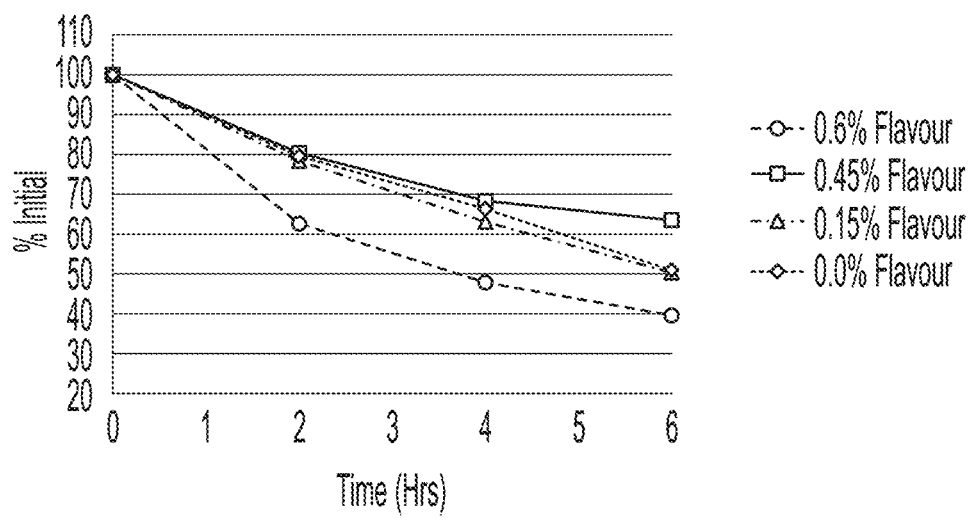
FIG. 3 shows a graph providing an evaluation of d90 particle size of hydrophobic coated API particles with various concentrations of liquid flavor.

FIGS. 1, 2, and 3 show the decrease in particle size (d10, d50, and d90, respectively) of hydrophobic coated API particles in a pharmaceutical suspension comprising various concentrations of liquid orange flavor. Ibuprofen was used as a model API. A particle size expressed in terms of its d10 means that 10 percent of the particles in a given volume of sample lie below a given particle size. Accordingly, a d50 particle size represents 50 percent of the particles in a given volume of sample lie below a given particle size, and a d90 particle size represents 90 percent of the particles in a given volume of sample lie below a given particle size. Specifically, FIGS. 3-5 show test results for suspension formulations containing hydrophobic coated API and liquid orange flavor at concentrations including 0.0%, 0.15%, 0.45%, and 0.60% w/w, held over a period of up to 6 hours with low shear mixing.

At concentrations of up to 0.45% w/w of orange flavor (including 0.15% w/w), the decrease in d10, d50, and d90 particle size within the first 2 hour "processing window" is largely similar to that of a suspension comprising hydrophobic coated API particles without any liquid flavor (0% liquid flavor). However, at a concentration of 0.6% w/w liquid orange flavor, the coating of the hydrophobic coated API particles is readily removed and a rapid decrease in particle size is observed. Further, at a liquid orange flavor concentration of 0.3% w/w, the aeration of the pharmaceutical suspension was sufficiently low with only little, if any damage to the coating of the coated API particle, and only minimal decrease in particle size of the hydrophobic coated API particles.

Example 3

Figure 4:
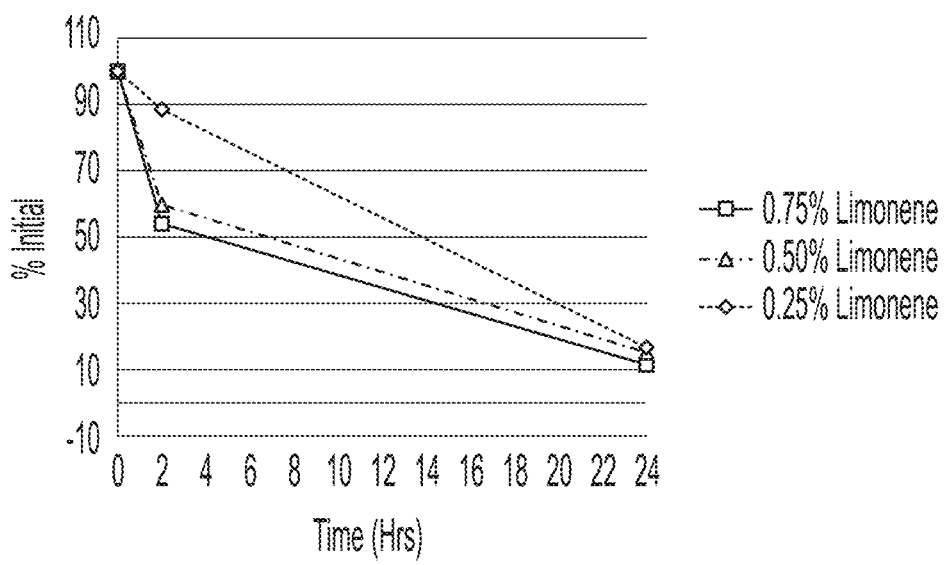
FIG. 4 shows a graph providing an evaluation of d10 particle size of hydrophobic coated API particles with various concentrations of pure limonene.
Figure 5:
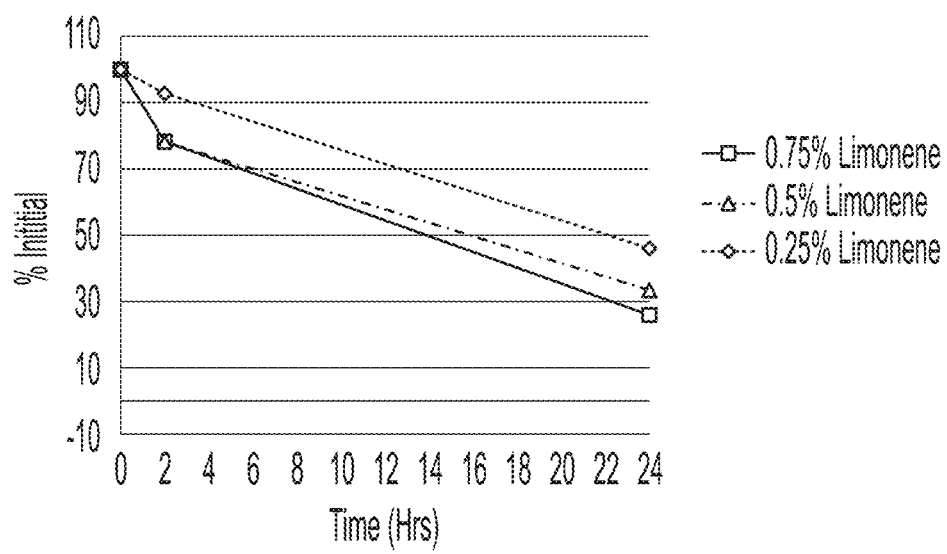
FIG. 5 shows a graph providing an evaluation of d50 particle size of hydrophobic coated API particles with various concentrations of pure limonene.
Figure 6:
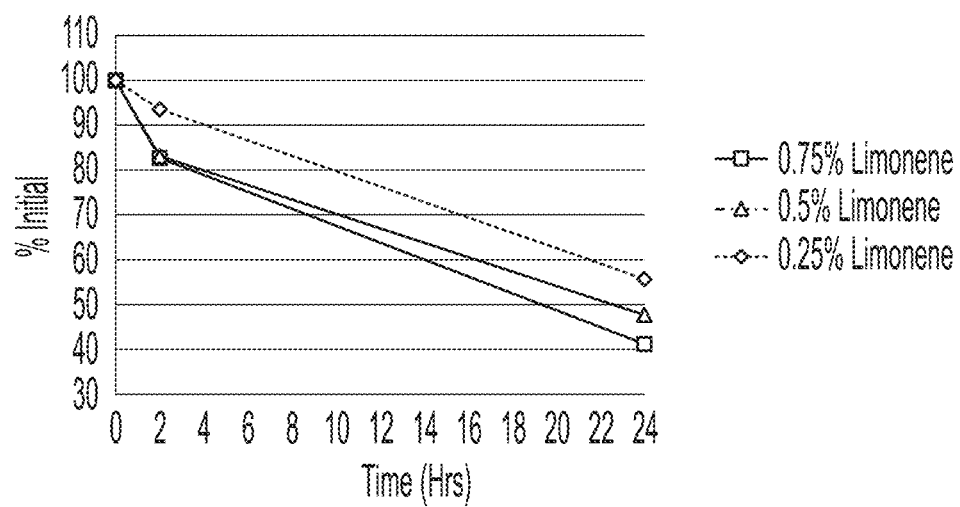
FIG. 6 shows a graph providing an evaluation of d90 particle size of hydrophobic coated API particles with various concentrations of pure limonene.
Figure 7:
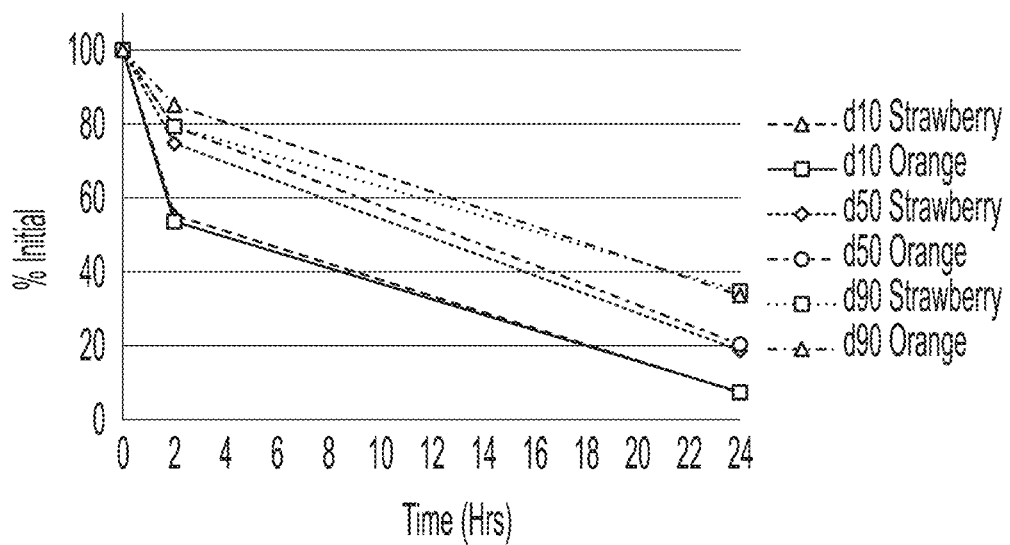
FIG. 7 shows a graph comparing the various particle size analyses of hydrophobic coated API with strawberry and orange liquid flavors.

FIGS. 4, 5, and 6 provide data on the decrease in d10, d50, and d90 particle size, respectively, of the hydrophobic coated API particles for the specific component limonene, which is found in some liquid flavors. These tests were conducted to explore the behaviors of the specific component of the liquid flavor, limonene, on hydrophobic coated API particles in suspension. Ibuprofen was used as a model API. Note that the concentrations of limonene shown in the Figures are significantly greater than the concentration of limonene that would be present if a liquid flavor was used. In FIGS. 6-8, pure limonene was used in concentrations of 0.25% w/w, 0.45% w/w, and 0.75% w/w and tested over a period of 24 hours. As shown across all three Figures, a limonene concentration of 0.25% w/w had a much less deleterious effect on the coating of the hydrophobic coated API particle size than limonene concentration of 0.45% w/w and 0.75% w/w. Further, the pharmaceutical suspensions tested with 0.25% w/w limonene comprised a sufficiently low amount of aeration. Accordingly, these tests confirm that limonene of the liquid orange flavor tested in FIGS. 3-5 are at least partially responsible for minimizing the aeration of the pharmaceutical suspension and subsequently eroding the coating of the hydrophobic coated API particles in relatively high quantities and/or at relatively high exposure times.

Example 4

FIG. 7 shows testing data of two different liquid flavors—strawberry and orange. D10, d50, and d90 particle sizes of the hydrophobic coated API particles were tested for both strawberry liquid flavor and orange liquid flavor. Both strawberry and orange liquid flavors comprise limonene. Ibuprofen was used as a model API. As shown in the Figure, both flavors behave similarly with regards to hydrophobic coated API particle size. The d10 particle samples showed a greater amount of particle size decrease within the first two hours of the trial than the d50 and d90 particle size samples. The d50 and d90 particle size samples exhibited less of a particle size decrease within the same two-hour period. However, this observation is consistent with the data of d10, d50, and d90 particle sizes of the previously-discussed examples.

Additionally, it was observed in all trials that as the particle size of the hydrophobic coated API (ibuprofen) particles decreased, a separate population of particles comprising a particle size of 5 μm to 20 μm appeared and increased with time. These particles are believed to be non-deformable coating material particles embedded within the deformed, continuous coating material prior to erosion of the coating due to shear forces. Accordingly, as the coating erodes, and the particle size of the hydrophobic coated API particles decreases, the population size of these smaller particles increases as the deformed coating material surrounding them erodes, causing these non-deformable particles to release from the hydrophobic coated API particles.

Overall, these trials show that by optimizing the amount of the terpene limonene to add to the pharmaceutical suspension comprising hydrophobic coated API particles, the amount of aeration in the suspension can be minimized to permit downstream processing while at the same time not having an adverse effect on the coating of the hydrophobic coated API particles (as determined by the particle size of the hydrophobic coated API particles.)

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A method of making a pharmaceutical composition comprising:
    providing a matrix solution/suspension comprising a matrix former, a structure former, anti-aerating agent, and a solvent; and
    mixing a plurality of hydrophobic coated active pharmaceutical ingredient (API) particles into the matrix solution/suspension to form a pharmaceutical suspension comprising 0.1% w/w to less than 0.6% w/w of the anti-aerating agent, wherein the plurality of hydrophobic coated API particles comprises greater than 70% w/w and no more than 90% w/w of API, and wherein the mixing comprises mixing for at least 2 hours and up to 6 hours, such that a particle size (d50) of the hydrophobic coated API particles decreases no more than 30% over the first 2 hours of the mixing;
    dosing the pharmaceutical suspension into preformed blister packs, wherein a dosed weight of the dosed pharmaceutical suspension is within 10% of a target dosed weight.

2. The method of claim 1, wherein the dosed weight of the dosed pharmaceutical suspension is within 5% of a target dosed weight.

3. The method of claim 1, wherein the dosed weight of the dosed pharmaceutical suspension is within 2.5% of a target dosed weight.

4. The method of claim 1, wherein the coated API comprise one or more of anti-inflammatoires, analgesics, anti-psychotics, anti-emetics, laxatives, anti-diarrheals, anti-histamines, or anti-depressants.

5. The method of claim 1, wherein the matrix solution/suspension comprises a viscosity modifier.

6. The method of claim 5, wherein the viscosity modifier comprises xanthan gum.

7. The method of claim 1, wherein mixing a plurality of hydrophobic particles into the matrix solution/suspension comprises in-line mixing at 15-20° C. degrees Celsius.

8. The method of claim 1, wherein the anti-aerating agent comprises one or more of a terpene or a terpinol.

9. The method of claim 1, wherein the anti-aerating agent comprises limonene.

10. The method of claim 1, wherein the matrix solution/suspension or pharmaceutical suspension comprises from 2.0-5.0% w/w matrix former.

11. The method of claim 1, wherein the matrix suspension/solution or pharmaceutical suspension comprises from 1.0-5.0% w/w structure former.

* * * * *